United States Patent [19]
Barber

[11] 3,936,502
[45] Feb. 3, 1976

[54] COPPER COMPOUND CATALYSTS FOR HYDRATION OF NITRILES TO AMIDES
[75] Inventor: William Austin Barber, Stamford, Conn.
[73] Assignee: American Cyanamid Company, Stamford, Conn.
[22] Filed: Oct. 30, 1972
[21] Appl. No.: 302,363

[52] U.S. Cl.......... 260/561 N; 260/404; 260/557 R; 260/558 R; 260/561 HL; 260/561 R
[51] Int. Cl.²...................................... C07C 103/08
[58] Field of Search.............................. 260/561 N

[56] References Cited
UNITED STATES PATENTS

| | | | |
|---|---|---|---|
| 3,381,034 | 4/1968 | Greene | 260/561 N X |
| 3,758,578 | 9/1973 | Habermann et al. | 260/561 N |
| 3,763,235 | 10/1973 | Newcombe et al. | 260/561 N X |
| 3,767,706 | 10/1973 | Habermann et al. | 260/561 N |

OTHER PUBLICATIONS

Ukhin et al., C. A., Vol. 71:61514h.
Watanabe, Bulletin Chem. Soc. Japan, Sept. 1964, pp. 1325–1329.

Primary Examiner—Ethel G. Love
Attorney, Agent, or Firm—Gordon L. Hart

[57] ABSTRACT

Hydration of nitriles to amides by reaction of a selected nitrile with water in presence of a solid catalyst selected from copper acetylide or copper nitride is described. The reaction is carried out with the reaction mixture in liquid state contacting the solid catalyst which is preferably in finely divided particulate form. The specific examples describe catalytic hydration of acrylonitrile to make acrylamide.

3 Claims, No Drawings

COPPER COMPOUND CATALYSTS FOR HYDRATION OF NITRILES TO AMIDES

The invention relates to catalytic hydration of nitriles to produce corresponding amide products. For example, acrylamide is produced by hydration of acrylonitrile with water in presence of a selected heterogeneous solid catalyst.

A number of solid heterogeneous solid catalysts have been proposed for use in the catalytic hydration of nitriles with water in liquid phase to convert the cyano radical of the nitrile to the

radical, thereby producing an amide from the nitrile. Some typical solid catalysts that have been proposed for this use have been manganese dioxide, Raney copper, Urushibara copper, Urushibara nickel, oxides of copper, copper chromium oxide, etc. With only a few exceptions most of the proposed catalysts have proved to be too low in catalytic activity for use in commercial processes. It has been usually recognized in prior art that a selected heterogeneous catalyst having proved useful catalytic activity for hydration of any selected nitrile will similarly be found to catalyze the hydration of a much broader range of nitriles although rates and yields may vary with different selected nitriles.

According to the present invention we employ either copper acetylide ($Cu_2C_2$) or copper nitride, $Cu_3N$ as the heterogeneous solid catalyst for hydration of a nitrile with water in a liquid reaction mixture. A mixture of the selected nitrile and water, preferably with the nitrile in aqueous solution, is contacted at a selected reaction temperature with the solid catalyst for contact time sufficient to permit the catalytic conversion.

These solid catalysts are effective to improve the rate of hydration of a nitrile that is at least slightly soluble with water. In the detailed examples below, preferred embodiments are described using acrylonitrile in the catalytic reaction with water to make acrylamide but the process of the invention can be used for hydration of many other nitriles such as benzonitrile, acetonitrile, propionitrile, stearonitrile, methacrylonitrile, chloroacetonitrile, nitroacetonitrile, cyclohexanecarbonitrile, napthylacetonitrile, adiponitrile, terephthalonitrile, phthalonitrile, succinonitrile, crotononitrile, dicyanocyclobutane, and the like. In appropriate cases an alcohol or other suitable cosolvent can be used to improve solubility of the nitrile in water for making the reaction mixture.

The catalytic process of the invention is adaptable for both batch and continuous processing. The hydration catalysts are active in finely divided form as illustrated in the examples below, without the use of catalyst supports. The catalysts can also be prepared and used on catalyst supports such as alumina, carbon, kieselguhr and the like. In use, the solid catalysts can be slurried in the liquid reactants, or can be placed in a fixed-bed catalytic continuous reactor through which the liquid reactants are passed in contact with the solid catalyst material.

The only pressure needed for the reaction will be sufficient pressure to maintain a liquid phase of the reactants at the operating temperature. It is sufficient to maintain autogenic pressure as the liquid reaction mixture is heated to reaction temperature. Higher pressures may be used as desired.

The reaction rate is increased as the reaction temperature is increased but in some instances the production of unwanted by-products may also increase at higher temperatures. With the particular catalysts of the present invention an optimum operating temperature will usually be found in the range from about 30°C. to about 125°C.

It is preferred to operate with an excess of water and with sufficient water to solubilize all of the nitrile reactant but the hydration will proceed with any practical mixture of the reactants in any ratio. We prefer to use enough excess water to solubilize the amide product. The reaction rate will usually increase as the ratio of catalyst to reactants is increased and as the contact time is increased. The catalyst is effective in catalytic amounts. For batch processes it is preferred to use a slurry of the solid catalyst in the liquid reaction mixture and in continuous processing it is preferred to employ a fixed-bed or stirred-tank catalytic reactor. For a batch process the reaction can be carried out with from about 0.1 to about 10 grams catalyst per gram of nitrile and in continuous processing the reaction can be carried out with contact times from about 0.5 to about 10 hours. We define contact time for a continuous reaction as catalyst bed volume divided by the volume flow rate of the reaction mixture.

It is preferred to begin the catalytic process with freshly prepared, finely divided, catalyst to ensure maximum catalyst activity. In the examples below are described preferred methods for fresh catalyst preparation but copper acetylide or copper nitride catalysts prepared by other methods can be used.

Reaction conditions should be chosen to reduce excessive degradation of the reactants and products. For example, when a nitrile is used that has olefinic unsaturation in the molecule, e.g. acrylonitrile, it may be preferred to use a polymerization inhibitor such as hydroquinone or the like, in very small amounts in the liquid reaction mixture.

Following are specific examples which include the best mode presently contemplated for carrying out the invention, with detailed description of certain preferred embodiments of the invention.

EXAMPLE I

Copper nitrate trihydrate, 3.2 g, and 12.8 g hydroxylamine hydrochloride were dissolved in 120 ml water to give a pale green solution. Concentrated ammonia, 12.8 ml, was added to give a colorless to pale blue solution. Calcium carbide, 0.6 g, was added as a solid to the solution to precipitate a bright red copper acetylide which was separated and washed. In a test tube with 0.25 g of the copper acetylide solid was placed 5.3 ml of 5.66 per cent by wt. aqueous solution of acrylonitrile. The mixture was reacted for 1 hour at 57°C. The reaction gave 13.5% conversion of acrylonitrile to acrylamide (equivalent of 45% for 1 g catalyst) at the end of 1 hour, with some by-product β-hydroxy propionitrile.

EXAMPLE II

Six grams of anhydrous copper difluoride was placed in a tube furnace and heated to 280°C. in a stream of $NH_3$ gas (~300 cc/min). The white fluoride turned dark green color and after 3 hours, the sample was cooled and removed to give 4.3 g of dark green $Cu_3N$. One gram of $Cu_3N$ was used at a catalyst as in Example 1 with 5.3 ml of 5.66% acrylonitrile aqueous solution. A 12.5% conversion to acrylamide was obtained in 1 hour at 57°C. with only a small amount of β-hydroxy propionitrile by-product.

I claim:

1. A process for production of acrylamide by hydration of acrylonitrile comprising contacting said nitrile in the presence of water with a solid heterogeneous catalyst selected from copper acetylide and copper nitride.

2. A process defined by claim 1 wherein the selected catalyst is copper acetylide.

3. A process defined by claim 1 wherein the selected catalyst is copper nitride.

* * * * *